United States Patent [19]

Pan et al.

[11] Patent Number: 5,024,673
[45] Date of Patent: Jun. 18, 1991

[54] NITROANILINE DYES WITH A CYANO SUBSTITUENT GROUP

[75] Inventors: Yuh-Guo Pan, Stamford; Lana Hochman, Westport, both of Conn.

[73] Assignee: Clairol Incorporated, New York, N.Y.

[21] Appl. No.: 596,120

[22] Filed: Oct. 11, 1990

Related U.S. Application Data

[62] Division of Ser. No. 333,528, Apr. 4, 1989, Pat. No. 4,980,158.

[51] Int. Cl.$^5$ .............................................. A61K 7/13
[52] U.S. Cl. ......................................... 8/414; 8/405; 8/406; 8/408; 8/428
[58] Field of Search .................... 8/414, 405, 406, 408, 8/428

[56] References Cited

U.S. PATENT DOCUMENTS 3,909,190  9/1975  Saygin .................................. 558/394
4,098,812  7/1978  Lutz et al. ............................ 558/418

OTHER PUBLICATIONS

Chem. Abs., vol. 58 (1963), 9086e.

Wilshire, *Aust. J. Chem.*, 1967, vol. 20, pp. 2269–2273.
Appleton et al., *Aust. J. Chem.*, 1970, vol. 23, pp. 1667–1677.

*Primary Examiner*—Josephine Barr
*Assistant Examiner*—William S. Parks
*Attorney, Agent, or Firm*—Charles J. Zeller

[57] ABSTRACT

The novel dye compound

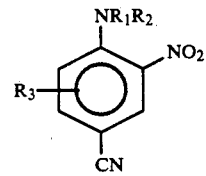

wherein $R_1$ and $R_2$, which may be the same or different are hydrogen, alkyl, hydroxyalkyl polyhydroxyalkyl, alkoxyalkyl, hydroxyalkoxyalkyl and amino alkyl, the alkyl group and the alkoxy group having from 1 to 6 carbons, and $R_3$ is a compatible substituent group, for example, hydrogen, alkyl, hydroxy, hydroxylalkyl and halogen. The dye compound is especially useful in hair dye compositions containing same.

9 Claims, No Drawings

NITROANILINE DYES WITH A CYANO SUBSTITUENT GROUP

This is a divisional application of U.S. Ser. No. 07/333,528 filed Apr. 4, 1989, now U.S. Pat. No. 4,980,158 issued Dec. 25, 1990.

FIELD OF INVENTION

The present invention concerns the novel dyes

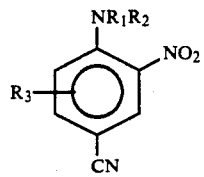

wherein $R_1$ and $R_2$, which may be identical or different, are hydrogen, alkyl, hydroxyalkyl, polyhydroxyalkyl, alkoxyalkyl, hydroxyalkoxyalkyl and aminoalkyl, each alkyl group and each alkoxy group having from about 1 to about 6 carbons, and $R_3$ is a compatible substituent group, for example, hydrogen, alkyl and halogen. More specifically, the present invention concerns the inclusion of the compound (I) in hair dye compositions as a direct dye, and especially the compound 4-(2-hydroxyethylamino)-3-nitrobenzonitrile, which species provides a yellow dye base for the hair dye composition.

BACKGROUND OF INVENTION

Nitro dyes, especially 2-nitroaniline derivatives, have long been used in the hair coloring art, including both oxidative and nonoxidative hair dye compositions. Such compositions typically include two or more hair dyes to provide a composite coloring effect to the hair. Depending on the shade desired, more or less of a yellow hair dye would be included. Indeed, in the dyeing of hair with a direct dye, it is necessary to provide dyes in admixture, to produce the natural shades desired.

A direct yellow dye of the prior art that is characterized by color fastness is

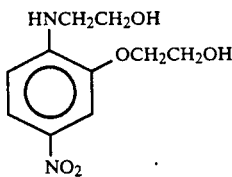

which compound is described in U.S. Pat. Nos. 4,337,061 and 4,417,896. Disadvantageously, the compound (II) has less than desirable light stability.

EP No. 182,330 discloses the direct dye

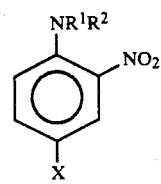

wherein $R^1$ and $R^2$ stand for H, $C_1$-$C_4$ alkyl, $C_2$-$C_4$ monohydroxyalkyl and $C_3$-$C_4$ dihydroxyalkyl, except that $R^1$ and $R^2$ do not simultaneously stand for $C_1$-$C_4$ alkyl radicals, and X is one of the radicals alkyl, monohydroxyalkyl, perfluoralkyl or halogen. Upon variation of the substituent X, the compound provides yellow shades ranging from blue-tinged lemon yellow to pure yellow to orange. Compound (III) when $R^1$ is $CH_2CH_2OH$; $R^2$ is hydrogen, and X is $CF_3$ has a much lower affinity for hair than Compound (I) when $R_1$ is $CH_2CH_2OH$, and $R_2$ and $R_3$ are hydrogen. Accordingly, a greater amount of the aforementioned Compound (III) is needed to obtain an equivalent color on hair.

SUMMARY OF INVENTION

It is an object of the present invention to provide novel dyes, especially, yellow direct dyes, suitable for incorporation in hair coloring compositions.

A primary object of the present invention is to provide yellow direct dyes suitable for coloring hair and having good light stability and washfastness.

Yet another aspect of the present invention is to provide a process for the synthesis of the direct cyanonitroamino dyes of the present invention.

The dyes of the present invention have the structural formula

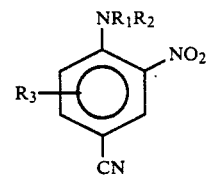

wherein $R_1$ and $R_2$, which may be identical or different, are hydrogen, alkyl, hydroxyalkyl, polyhydroxyalkyl, alkoxyalkyl, hydroxyalkoxyalkyl and aminoalkyl, each alkyl group and each alkoxy group having from about 1 to about 6 carbons, and $R_3$ is a compatible substituent group such as hydrogen, alkyl of 1 to about 6 carbons, hydroxyalkyls whose alkyl moiety has from about 1 to about 6 carbons, hydroxy and halogen, in particular, chlorine. It has been found that the compound (I) of the present invention is suitable to color hair and provides above-average light stability and washfastness.

Preferably, $R_1$ is $CH_2CH_2OH$; $CH_2CH_2OCH_2CH_2OH$, and $CH_2CH(OH)CH_2OH$, and $R_2$ and $R_3$ are hydrogen.

DETAILED DESCRIPTION OF THE INVENTION

The direct dyes of the present invention are suitable for incorporation in a hair dye or surface active agents composition comprising one or more of the following: solvents, surfactants or surface-active agents, thickeners, antioxidants, preservatives, fragrances, and other constituents typically employed in hair dye compositions. In addition, the dye composition may also contain one or more additional dye components, the admixture of dyes (including the dye of the present invention) providing the desired shade. The compositions of the present invention may also contain one or more hair conditioning agents. Such conditioning agents are typically cationic in character and include cationic surface-active agents and cationic polymeric materials. The dyes of the present invention might also be incorporated into an oxidation dye base, to obtain a desired shade.

The constituents includable in the hair dye compositions of the present invention are generally within the ranges tabulated below.

TABLE I

| Constituent | Broad Range Wt. % | Usual Range Wt. % |
| --- | --- | --- |
| Dye (I) | 0.001–5 | 0.01–1 |
| Other dyes | 0–10 | 0.01–4 |
| Surfactants | 0–25 | 0.1–5 |
| Thickening agents | 0–20 | 0.1–5 |
| Nonaqueous solvents | 0–40 | 1–10 |
| pH Modifiers | 0–20 | 0.05–5 |
| Fragrance | 0–5 | 0.05–1 |
| Water | <<< Q.S. 100% >>> | |

The compound (I) may be synthesized by reacting 4-chlorobenzaldehyde, sodium formate, hydroxylamine hydrochloride and formic acid to form 4-chlorobenzonitrile, which may be nitrated to form 4-chloro-3-nitrobenzonitrile. Finally, this compound is reacted with the appropriate amine to obtain the desired compound (I) of the present invention.

Specifically, the synthesis is illustrated by Example 1 below.

EXAMPLE 1

(a) 4-(2-hydroxyethylamino)-3-nitrobenzonitrile 4-chlorobenzaldehyde (50 g; 0.36 mol), sodium formate (48.4 g; 0.71 mol), and hydroxylamine hydrochloride (24.7 g; 0.36 mol) were added to 400 ml formic acid (98 wt. %). The reaction mixture was refluxed for 1 hour at 130° C., cooled to room temperature and poured into 1 liter cold water to produce a white precipitate, which was filtered and air-dried to yield 43 g 4-chlorobenzonitrile (m.p.=91°–92° C.). The yield for this step in the reaction sequence was about 88%.

The 4-chlorobenzonitrile prepared above (40 g; 0.29 mol) was added to 100 ml fuming nitric acid (90%) and 75 ml concentrated sulfuric acid was then added slowly to this reaction mixture over a period of 45–60 minutes via a dropping funnel at 10°–20° C. in an ice bath. After one hour, with constant stirring, the reaction mixture was poured into an ice water bath to obtain a pale yellow precipitate, which was filtered and washed several times with cold water, and air-dried. The yield was 51.6 g (97%) 4-chloro-3-nitrobenzonitrile (m.p.=97°–99° C.).

Monoethanolamine (38 ml; 0.62 mol) was added to a suspension of 4-chloro-3-nitrobenzonitrile (51.6 g; 0.28 mol) in 270 ml water. The reaction mixture was refluxed for one hour at 100°–110° C. (oil bath). After cooling to room temperature, the orange precipitate was filtered, washed with water and air-dried to give 55.8 g 4-(2-hydroxyethylamino)-3-nitrobenzonitrile (m.p.=132°–134° C.). The yield was about 95%, with the overall yield for the reaction sequence, illustrated below, being about 81%.

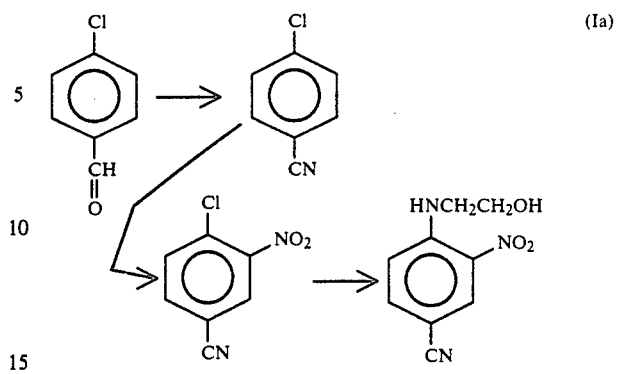

(b) 4-[2-(2-hydroxyethoxy)ethylamino]-3-nitrobenzonitrile

Preparation is similar to the synthesis in (a) above, except that 2-(2-aminoethoxy)ethanol is used in lieu of monoethanolamine.

(c) 4-(2,3-dihydroxypropylamino)-3-nitrobenzonitrile

Preparation is similar to the synthesis in (a) above, except that 3-amino-1,2-propanediol is used in lieu of monoethanolamine.

The Compounds (Ia), (Ib) and (Ic) have the following properties:

TABLE II

| Compound | $\lambda_{max}$ | $\epsilon$ | $\gamma$ |
| --- | --- | --- | --- |
| Ia | 412 | 5,700 | 3.1 |
| Ib | 412 | 3,900 | — |
| Ic | 414 | 4,800 | 2.0 |
| II | 398 | 16,000 | 2.3 |
| IIIa[1] | 410 | 5,400 | 1.3 |

Note:
[1] Dye IIIa is the dye III shown at page 3 when $R^1$ is $CH_2CH_2OH$; $R^2$ is hydrogen and X is $CF_3$.

$\lambda max$ is the absorbance maxima for the dye, the values for the dyes in Table II being characteristic of a yellow color. $\epsilon$ is the molar extinction coefficient and is calculated from the equation ab/c wherein a is the absorbance maxima, b is the cell length (cm) and c is the concentration in g/cc in 95% ethanol. The extinction coefficient is a measure of the intensity of color produced by a dye compound. $\gamma$ is the partition coefficient, which is the ratio:

$$\gamma = \frac{\text{mg dye/g hair}}{\text{mg dye/g dye bath}}$$

In the above equation, the weight of dye absorbed by hair is determined from a hair tress that has soaked in a dye bath of known dye concentration for 24 hours. The partition coefficient is, thus, a measure of the affinity of a dye for hair fibers.

It is seen from the values in Table II that dye (II) has an extremely high extinction coefficient—three times higher than that for the compound Ia. Thus, Compound II imparts a very intense color to solutions containing same. Yet it is seen, surprisingly and unexpectedly, that compound (Ia) of the present invention has a partition coefficient that is 35% greater than that of dye (II) and 138% greater than the dye IIIa. Thus, even though not as intense as dye (II), the dye (Ia) of the present invention is seen to enjoy a substantially superior affinity for hair.

In practice, the dyes employed in this invention would most often be used with other dyes. The amount of the dyes used would depend on the lightness or darkness of the desired shade, as well as on the desired tonality.

In carrying out the present invention, any of the benzonitrile dyes described above or combinations thereof are incorporated in a fluid hair dye vehicle of the type suitable for applying direct-dyeing dyes. A large number of such vehicles are known to those in this art. These may vary from simple aqueous solutions and/or suspensions of the dye to very sophisticated aqueous compositions such as creams, mousses, lotions, pastes, gels, and the like. Often, the compositions of the present invention contain, in addition to the subject dyes herein disclosed, a second dye or a blend of other dyes, nonionic and anionic surfactants, solvents, thickeners, antioxidents, preservatives, fragrances, etc. In these aqueous compositions, the carriers or vehicles may be water or a combination of water with other solvents, e.g., ethanol. It may also be employed in an aerosol system, e.g., an aerosol emulsion system in which the dye is contained in an aqueous phase of the system. See, for example, U.S. Pat. No. 4,021,486 to Halasz, et al.

The benzonitrile dyes employed in the present invention can be employed to prepare basic, neutral or acidic dye compositions. Furthermore, they may likewise be included in hair dyeing compositions which contain other direct dyeing dyes. A variety of direct dyeing dyes is known in the prior art which are useful for this purpose. They include nitro dyes, azo dyes, anthraquinone dyes, etc. By way of illustration, any of the nitro dyes disclosed in the following U.S. Patents may be used in conjunction with the present dyes: U.S. Pat. Nos. 2,750,326; 2,750,327; 3,088,877; 3,088,878; 3,088,978; 3,642,423; 3,950,127; 4,125,601; 4,432,769, and 4,337,061.

The pH of the present dye compositions can vary from about 4 to 12 and preferably from 7 to 11.5, and may be obtained by adjustment with a suitable pH modifying agent. The compositions herein may also contain buffering agents which maintain the pH within a particular range.

When the compositions are to be basic, an alkalizing agent can be employed over a wide range, depending on the dye and particular alkalizing agent employed and the desired pH. Illustratively, the alkalizing agent can vary between zero to about 20%, preferably from about 0.05 to about 5%, and most preferably from about 0.10 to about 2%, by weight of the composition. Any of a wide variety of alkalizing agents can be used to adjust the pH of the present dyeing composition on the basic side. Ammonium hydroxide, because of its freedom from toxicity over a wide concentration range and its economy, is an acceptable alkalizing agent. However, there can be used in place of, or together with, ammonia any other compatible ammonia derivative as an alkalizing agent, such as an alkylamine, e.g., ethylamine, dipropylamine, or triethylamine; an alkanediamine, e.g., 1,3-diaminopropane; an alkanolamine, e.g., monoethanolamine or diethanolamine, triethanolamine, a polyalkylene polyamine, e.g., diethylenetriamine; or a heterocyclic amine, such as morpholine.

The pH of the composition may be adjusted on the acid side with any inorganic or organic acid or acid salt which is compatible with the composition and will not introduce toxicity under its conditions of use, especially when acid compositions are desired. Illustrative of acids or acid salts there can be mentioned; sulfuric, formic, acetic, oleic, lactic, citric or tartaric acid, or ammonium sulfate, sodium dihydrogen phosphate or potassium bisulfate. Illustratively, the acidifying agent is from about zero to about 5%, and preferably from about 0.05 to about 1%. Together, the alkalizing, acidifying and buffering agents are referred to herein as pH modifiers.

Surface active agents can also be employed in the dyeing compositions of this invention. These can be anionic, nonionic or cationic. By way of examples of the various types of surface active agents, there can be mentioned: higher alkylbenzene sulfonates; alkylnaphthalenesulfonates; sulfonated esters of alcohols and polybasic acids; taurates; fatty alcohol sulfates; sulfates of branched chain or secondary alcohols; alkyldimethylbenzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester; myristyl sulfate; glyceryl monostearate; triethanolamine oleate, sodium salt of palmitic methyl taurine; cetyl pyridinium chloride; lauryl sulfonate; myristyl sulfonate; lauric diethanolamide; polyoxyethylene stearate; ethoxylated oleyl diethanolamide; polyethylene glycol amides of hydrogenated tallow; stearyldimethyl benzyl ammonium chloride; dodecylbenzene sodium sulfonate; 2-amino-2-methyl propanol; triethanolamine salt of p-dodecylbenzene sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isethionate; sodium dodecyl sulfate; the sodium salt of 3-O-diethyl tridecanol-6-sulfate and the like. The quantity of surface active agent can vary over a wide range, such as that of from about 0.05% to 15% and preferably from about 0.10 to 5% by weight of the composition.

A thickening agent may also be incorporated in the dyeing composition of this invention which may be one or several of those commonly used in hair dyeing. These are exemplified by such things as sodium alginate or gum arabic, or cellulose derivatives, such as methylcellulose, e.g., Methocel 60HG, or the sodium salt of carboxymethylcellulose, or hydroxyethylcellulose, e.g., Cellosize QP-40 or acrylic polymers, such as polyacrylic acid sodium salt, or inorganic thickeners, such as bentonite. The quantity of this thickening agent can also vary over a wide range, such as that of from about 0.1 to 20%. Ordinarily it will range from about 0.5 to 5% by weight of the composition. The viscosity of the composition may vary from about 1 cp to about 100,000 cps. For a typical lotion formulation, composition viscosity is between about 100 cps to about 10,000 cps.

It is also useful to incorporate an antioxidant in the present dye compositions. A variety of antioxidants are known in the prior art which would be useful for this purpose. Among these mention may be made of the inorgnaic sulfites, e.g., sodium sulfite, thioglycollic acid and other mercaptans, butylated hydroxytoluene, sodium dithionite, various forms of ascorbic acid and its derivatives, e.g., sodium ascorbate, erythorbic acid, ascorbyl palmitate, ascorbyl laurate, etc. The quantity of antioxidant when in use can vary quite a bit. However, this will, in general, be of the order of about 0.001 to 1% by weight.

The benzonitrile dyes are incorporated in compositions of this invention in tinctorially effective quantities, i.e., in concentrations which are adequate to color the hair. These quantities can vary over a wide range, but ordinarily they will constitute from about 0.001 to greater than about 5%, e.g., 10% by weight of the composition. However, preferably it will comprise from about 0.001 to about 2% by weight of the composition. The major constituent of the composition employed is usually water, and this can vary in amount over a wide range dependent in large measure on the quantity of other additives. Thus, the water content can be as little as 10%, but preferably will amount to from about 70 to 99% by weight of the composition.

The dyeing compositions of this invention are preferably aqueous compositions. The term aqueous composition is used herein in its usual generic sense as embracing any water-containing composition useful for the present purposes. This includes true solutions of the dye in an aqueous medium, either alone or in conjunction with other materials, which are also dissolved or dispersed in the aqueous medium. The term aqueous composition also encompasses any mixture of dye with the aqueous medium either alone or together with other ingredients. The dye may be colloidally dispersed in the medium or may merely be intimately mixed therein. Moreover, the aqueous medium may comprise water or water and an additional or auxilliary solvent. The latter may be employed as a common solvent to enhance the solubility of the dye or some other organic material. Other auxiliary solvents which may be used for this purpose include ethanol, carbitol, isopropanol, propylene glycol, ethylene glycol, diethylene glycol, diethylene glycol monoethyl ether, glycerine, etc.

The benzonitrile dye and any of the surface active agents, thickening agents, and combinations thereof set forth above may be used in the proportions specified in the Table I.

The aqueous dyeing compositions of this invention can be prepared by the conventional methods used in the hair dyeing art. Thus, they can be prepared by dissolving or suspending the dye in water in the desired concentrations. Water miscible organic solvents, e.g., ethanol, can be employed to facilitate solutions of the dye. In this event, the dye can be dissolved first in the solvent and this solution is then diluted with water. The dispersion of the various ingredients can also be facilitated by heating the composition at temperatures varying from 40° C. to 110° C., either before dilution with water or afterwards.

These compositions can be applied to hair by the conventional techniques used in this art. Illustratively, when applied to living hair on the human head, the compositions can be applied to the hair with a brush, sponge, or other means of contact, such as pouring the composition directly onto the hair until saturated. The reaction time or time of contact of the dyeing composition with the hair is not critical and can vary over a wide range used in the hair dyeing art, such as periods of about 5 minutes to about 2 hours. Preferably, a period of from about 5 minutes to about 60 minutes is utilized, and most often a period of 15 to 45 minutes. The dyeing temperature can vary over wide limits as is conventional in the art. Thus, the dyeing temperature can vary from about room temperature, e.g., about 20° to about 60° C., and preferably from about 20° to about 45° C. At the end of the time period, the composition is rinsed from the hair with water, although a weak acid solution may be employed.

EXAMPLE 2

The following compositions were prepared.

TABLE II

| Constituent | Concentration, Wt. % | |
|---|---|---|
| | 2-A | 2-B |
| Dye (Ia) | 0.10 | 0.25 |
| Surface-active agents | 5.32 | 5.32 |
| Organic solvents | 5.00 | 5.00 |
| Thickeners | 1.35 | 1.35 |
| pH modifiers | 0.98 | 0.98 |
| Antioxidants | 0.28 | 0.28 |
| Fragrances | 0.12 | 0.12 |
| Water | << Q.S. 100% >> | |

Compositions 2-A and 2-B were each used to dye bleached and blended gray hair tresses. The tresses were soaked in the hair dye solution for 30 minutes, rinsed with water, and dried.

The tresses were then subjected to a series of five shampoos to determine washfastness. The Hunter Tristimulus values of the original, dyed, and shampooed hair tresses are recorded in Table III below.

TABLE III

| | Hunter Tristimulus Values | | | | | |
|---|---|---|---|---|---|---|
| | Composition 2-A | | | Composition 2-B | | |
| Tress | L | a | b | L | a | b |
| Bleached Tresses | | | | | | |
| Original | 58.21 | 1.73 | 16.23 | 58.21 | 1.73 | 16.23 |
| Color on Hair | 53.82 | −1.94 | 24.51 | 52.61 | −3.12 | 28.76 |
| Shampooed | 53.76 | 0.79 | 16.64 | 54.59 | 0.14 | 17.03 |
| Blended Gray Tresses | | | | | | |
| Original | 34.84 | −0.17 | 6.97 | 34.84 | −0.17 | 6.97 |
| Color on Hair | 32.47 | −1.77 | 11.14 | 31.78 | −2.92 | 14.30 |
| Shampooed | 32.21 | −0.87 | 8.65 | 32.50 | −1.77 | 11.01 |

In the Hunter Tristimulus System, L is a measure of lightness and darkness, that is, the depth of the color of the hair tress. The lower the value of L, the darker the color.

A decrease in the value of L indicates a darkening of the hair tress. In the case of bleached and blended gray hair, a lowering of L shows deposition of hair dye on the tress.

It is seen that both the bleached and blended gray hair tresses were colored to a substantial degree by the dye (Ia). Moreover, it is seen that the shampooings did not increase the values of L in the several tests, indicating good washfastness for the dye (Ia).

The a value is a measure of the greenness or redness of the hair's color. As the a value increases, the hair has a more prominent red tonality. A lowering in the a value results in greener shades. The data in Table III shows that the dye (Ia) provides green nuances to the hair tress.

The value of b is a measure of the blueness or yellowness of the hair color. As the b value increases, the hair tress is more yellow. It is seen that the tresses dyed with the dye (Ia) enjoy a substantial increase in the value of b.

Based on these results, it is seen that dye (Ia) would be quite suitable in a semipermanent hair dye composition.

EXAMPLE 3

The 4-(2-hydroxyethylamino)-3-nitrobenzonitrile [Dye (Ia)] compositions, one for use as a light ash brown shade and the other as a dark brown shade.

TABLE III

| Constituent | Concentration, Wt. % | |
| --- | --- | --- |
| | Lt. Ash Brown | Dark Brown |
| Dye (Ia) | 0.0947 | 0.1300 |
| Other dyes | 0.2962 | 2.9355 |
| Surface active agents | 5.3220 | 4.4400 |
| Organic solvents | 5.0000 | 5.0000 |
| Thickeners | 1.3500 | 1.3500 |
| pH modifiers | 0.9800 | 1.9600 |
| Antioxidants | 0.2763 | 0.2695 |
| Fragrance | 0.1225 | 0.0980 |
| Water | << Q.S. 100% >> | |
| Total | 100% | 100% |

Each of the two compositions above was used to dye blended gray and commercially bleached hair swatches, by allowing the swatches to soak in the dye compositions for about 30 minutes, after which the swatches were rinsed in water and dried.

Table III shows that Dye Ia can be used in combination with other hair dyes in the increased base to give a wide range of desirable shades.

We claim:

1. A hair dye composition comprising 0.001 to 5% of a cyano substituted nitroaniline dye compound having the structure

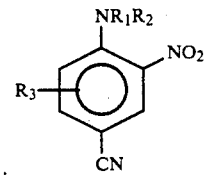

(I)

wherein $R_1$ and $R_2$ are each selected from the group consisting of hydrogen, alkyl, hydroxyalkyl, polyhydroxyalkyl, alkoxyalkyl, hydroxyalkoxyalkyl and aminoalkyl, and $R_3$ is selected from the group consisting of hydrogen, alkyl, hydroxy, hydroxyalkyl and halogen, the alkyl and alkoxy moieties having from 1 to about 6 carbons; from about 0.01 to about 10% of one or more other dye compounds, and an aqueous vehicle as the remainder.

2. The hair dye composition of claim 1 further comprising one or more of the following: surface-active agents in an amount up to about 25%; thickening agents in an amount up to about 20%, nonaqueous solvents in an amount up to about 20%, and fragrance in an amount up to about 5%.

3. The hair dye composition of claim 2 wherein the concentrations of the recited constituents are as follows: 0.01–4% other dyes, 0.1–5% surface-active agent, 0.1–5% thickening agent, 1–10% nonaqueous solvent, 0.05–5% pH modifier, and 0.05–1% fragrance.

4. The hair dye composition of claim 3 wherein the hair dye is 4-(2-hydroxyethylamino)-3-nitrobenzonitrile.

5. The hair dye composition of claim 3 wherein the hair dye is 4-(2,3-dihydroxypropylamino)-3-nitrobenzonitrile.

6. The hair dye composition of claim 3 wherein the hair dye is 4-[2-(2-hydroxyethoxy)ethylamino]-3-nitrobenzonitrile.

7. The hair dye composition of claim 3 in the form of a lotion having a viscosity between 100 and 10,000 cps.

8. A method of dyeing hair comprising the step of applying to the hair the composition of claim 1 or 3.

9. The method of claim 8 wherein the dye compound (I) is 4-(2-hydroxyethylamino)-3-nitrobenzonitrile.

* * * * *